United States Patent

Edelman

[11] Patent Number: 5,846,197
[45] Date of Patent: Dec. 8, 1998

[54] COMPENSATING FOR MAGNETIZATION TRANSFER EFFECTS IN MULTISLICE AND THREE-DIMENSIONAL MRI BLOOD FLOW MAPPING STUDIES

[75] Inventor: Robert R. Edelman, Newton, Mass.

[73] Assignee: Beth Israel Deaconess Medical Center, Boston, Mass.

[21] Appl. No.: 40,234

[22] Filed: Mar. 16, 1998

[51] Int. Cl.⁶ .................................................... A61B 5/05
[52] U.S. Cl. .................. 600/419; 324/306; 324/307; 324/309
[58] Field of Search .................................. 600/410, 419; 324/306, 307, 309

[56] References Cited

U.S. PATENT DOCUMENTS

| Re. 34,495 | 1/1994 | Sano et al. | 128/653.3 |
|---|---|---|---|
| 4,849,697 | 7/1989 | Cline et al. | 324/306 |
| 4,915,111 | 4/1990 | Sano et al. | 128/653 AF |
| 4,947,847 | 8/1990 | Sano et al. | 128/653 AF |
| 5,277,182 | 1/1994 | Koizumi et al. | 128/653.3 |
| 5,285,158 | 2/1994 | Mistretta et al. | 324/309 |
| 5,307,014 | 4/1994 | Laub | 324/306 |
| 5,588,431 | 12/1996 | Mani et al. | 128/653.3 |
| 5,627,468 | 5/1997 | Kojima et al. | 324/307 |
| 5,671,742 | 9/1997 | Dumoulin et al. | 128/653.3 |

*Primary Examiner*—Marvin M. Lateef
*Assistant Examiner*—Eleni Mantis Mercader
*Attorney, Agent, or Firm*—Mark H. Jay

[57] ABSTRACT

To compensate for magnetization transfer effects that result from use of a labeling pulse to label inflowing blood, at least two control pulses are used. The control pulses have a total compensating flip angle that equals the flip angle of the labeling pulse, and are applied to the same volume to which the labeling pulse is applied. Advantageously, the labeling and control pulses are adiabatic.

13 Claims, 4 Drawing Sheets

COMPENSATING FOR MAGNETIZATION TRANSFER EFFECTS IN MULTISLICE AND THREE-DIMENSIONAL MRI BLOOD FLOW MAPPING STUDIES

BACKGROUND OF THE INVENTION

The invention relates to magnetic resonance imaging (MRI), and more particularly relates to MRI blood flow mapping studies such as are used to map blood flow in the human brain. In its most immediate sense, the invention relates to compensating for magnetization transfer effects in multislice and three-dimensional MRI blood flow mapping studies.

In a known type of MRI blood flow mapping study, blood flow is mapped by acquiring two MR images of the slice of interest and comparing them (as by subtraction). To form the first image, inflowing blood is labeled and MR data are acquired from a slice of interest with the labeled blood present therein. The second image is reconstructed from MR data acquired from the same slice in which inflowing blood has not been so labeled. Because the blood spins have been labeled and the surrounding tissues have not, such a subtraction causes the image of the stationary tissue to cancel out and therefore highlights the blood flow.

Labeling of the blood may conventionally be accomplished by using an RF labeling pulse that inverts the arterial spins of the blood in a predetermined volume that is upstream of the slice of interest. When this technique is employed, it is sometimes (e.g. in the case of studies of the human brain) necessary to compensate for magnetization transfer effects.

Magnetization transfer effects cause the labeling pulse to affect the entire volume (and not merely the predetermined volume where the blood spins are inverted or on the slice of interest that is to be imaged). As a result, without compensation for such effects, subtraction between the above-described two images will produce an incomplete cancellation of the stationary tissue. As a result, it is necessary to compensate for such effects.

In the past, and especially in e.g. MR studies of the human brain, magnetization transfer effects have been compensated by applying a second RF pulse (referred to as a control pulse) before acquiring the MR data for the second image of the slice of interest. This control pulse has a flip angle that is identical to the labeling pulse, and is applied to another volume that is arterially downstream of, and equidistant from, the slice of interest. Because of the magnetization transfer effect, the control pulse also affects the entire volume, just as the labeling pulse previously did. Furthermore, because the slice of interest is equidistant from both volumes, and because the flip angles of the labeling and control pulses are the same, they have an identical effect on the slice of interest. As a result, the above-referenced subtraction causes the stationary tissue to cancel out.

Although this compensation technique works well for single-slice studies, the technique is unsuitable for use in multislice studies and three-dimensional studies. This is because the labeling and control pulses only have identical effects at the slice of interest. At other locations within the volume of interest, the pulses have different effects, and image subtraction does not cancel these effects out. Hence, use of labeling pulses in multislice and three-dimensional studies causes magnetization transfer effects for which compensation has until now been unavailable.

Accordingly, one object of the invention is to provide a method for compensating magnetization transfer effects in multislice and three-dimensional blood flow mapping studies.

Another object is to provide such a method that is suitable for mapping blood flow in the human brain.

Still a further object is, in general, to improve on methods of this general type.

In accordance with the invention, a conventional control pulse is replaced with at least two control pulses. The control pulses have a total compensating flip angle equalling the flip angle of the labeling pulse. And, the control pulses are applied to the same volume where the labeling pulse is applied.

Because the flip angle of the labeling pulse is the same as the total flip angle produced by the control pulses, and because all the pulses are applied to the same volume, the effect of the labeling pulse at any location within the volume of interest is the same as the total effect of all the control pulses at that location. Accordingly, the magnetization transfer effect is compensated throughout the volume of interest. Because this compensation is not localized, multislice studies and three-dimensional studies can be compensated for magnetization transfer effects.

A conventional labeling pulse is a 360° adiabatic pulse, i.e. is a pulse with a 360° flip angle that produces a 180° inversion of the blood spins. Where such a labeling pulse is used, and in accordance with the preferred embodiment of the invention, there are two adiabatic control pulses, each having a 180° flip angle. In this preferred embodiment, the second control pulse re-inverts the already-inverted blood spins, so as to essentially restore the blood spins to their original uninverted direction. Hence, the second acquisition of MR data are carried out when the slices or three-dimensional slabs of interest contain uninverted blood spins.

Advantageously, the invention can be used in a two- or three-dimensional MR pulse sequence of a motion-insensitive type, i.e. a two-dimensional or three-dimensional echo-planar sequence.

BRIEF DESCRIPTION OF THE DRAWINGS

The invention will be better understood with reference to the accompanying exemplary and non-limiting drawings, in which.

DETAILED DESCRIPTION OF PREFERRED EMBODIMENTS

Figure 1:
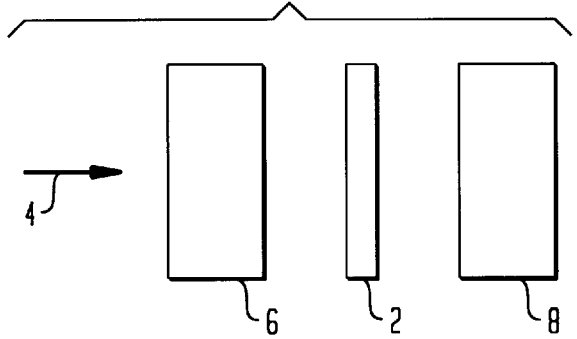
FIG. 1 schematically illustrates a conventional single-slice MR blood flow mapping study in which the effects of magnetization transfer are compensated.

In a single-slice MR bloodflow mapping study such as is schematically illustrated in FIG. 1, MR data are acquired twice from the slice 2 of interest. During one acquisition (which is usually but not necessarily the first one) the spins of inflowing blood (the direction of bloodflow is indicated by reference number 4) are inverted before the blood reaches the slice 2, so that the acquired MR data reflects inverted blood spins. During the other acquisition, inflowing blood spins are not inverted. Therefore, when MR images are reconstructed from these acquisitions and subtracted (or otherwise compared), the stationary tissue cancels out and the distribution of the blood within the slice 2 is highlighted.

Figure 2A:
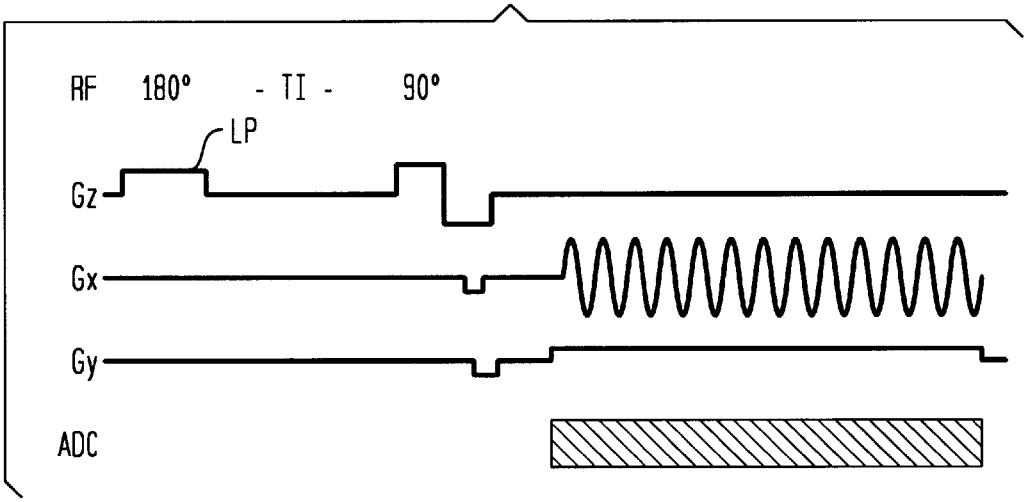
FIGS. 2A and 2B schematically illustrate, respectively, the use of a labeling pulse and the use of a control pulse in a conventional two-dimensional MR pulse sequence used for the study illustrated in FIG. 1.
Figure 2B:
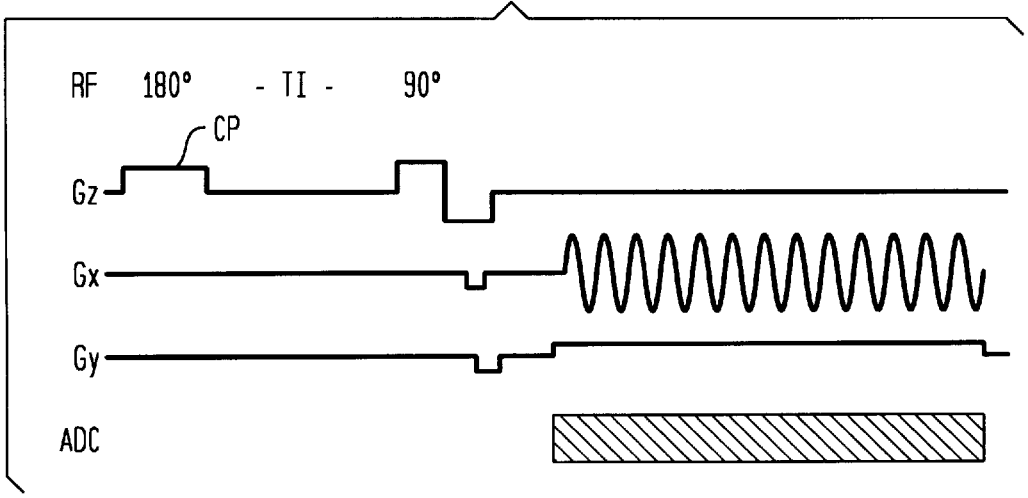

Conventionally, inversion of the blood spins is accomplished using an RF pulse (known as a labeling pulse, and shown as LP in FIG. 2A) that is applied to a volume 6 arterially upstream of the slice 2. (Conventionally, as in the two-dimensional EPISTAR echo planar pulse sequence that is available on MR imagers produced by Siemens AG of Germany, and that is shown in FIGS. 2A and 2B, the labeling pulse is a 180° RF pulse.) Some time (TI, in FIGS. 2A and 2B) later, when the thus labelled or "tagged" blood spins reach the slice of interest 2, MR data are acquired. The next acquisition is carried out after the affects of the labeling pulse LP have died out, MR images are reconstructed from both acquisitions, and one image is then subtracted from the other. In circumstances where the magnetization transfer effect is not significant, this subtraction highlights the regions of blood flow, because stationary tissue in the two images is depicted with the same intensity in each of the images and cancels out.

However, in regions (e.g. the human brain) where magnetization transfer effects are pronounced, this conventional technique produces unsatisfactory results. This is because the magnetization transfer effect causes the labeling pulse LP to have nonlocalized effects; it affects not only the volume, but the entire volume of interest, including the slice 2. Hence, the stationary tissue in the two images is not shown with the same intensity in each, and does not cancel out when one image is subtracted from the other. This reduces the diagnostic value of the resulting subtraction image.

Conventionally, for e.g. brain studies in which the magnetization transfer effect plays a significant part, the effect is compensated by using an RF control pulse CP (see FIG. 2B) before the second MR data acquisition. This control pulse CP is applied to volume 8, so as not to invert blood spins that flow into the slice 2. And, the volume 8 is selected so that the slice 2 is equidistant between the volume 6 and the volume 8. Because the slice 2 is equidistant from the volumes 6 and 8 and the magnetization transfer effect is the same for the labeling pulse LP and the control pulse CP, the control pulse CP has the same effect on the slice 2 as does the labeling pulse LP. For this reason, the intensity of the stationary tissue is the same in both reconstructed images, and subtracting one image from the other cancels out the stationary tissue.

While this known compensation technique works properly with single slice studies, it does not work for multislice or three-dimensional studies. (In a multislice study, a three-dimensional image of a volume of interest is formed by acquiring a series of two-dimensional images that relate to adjacent slices of the volume of interest. In a three-dimensional study, a three dimensional image of a slab of the volume of interest is formed directly.) The reason for this is shown in FIG. 3 (which relates to a multislice study) and FIG. 4 (which relates to a three-dimensional study).

Figure 3:
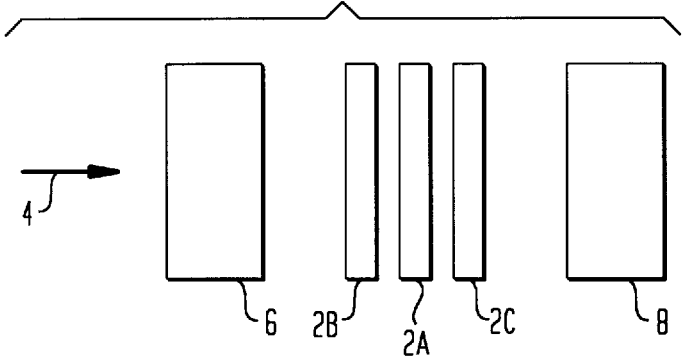
FIG. 3 schematically illustrates how a conventional magnetization transfer compensation scheme fails to compensate for magnetization transfer effects when used in a multislice MR study.

Considering FIG. 3 first, it will be seen that although the slice 2A is midway between the volumes 6 and 8 and that the magnetization transfer effect is consequently compensated at that slice 2A, the slices 2B and 2C are not equidistant from the volumes. The slice 2B is closer to the volume 6 (where the labeling pulse LP is applied) and the slice 2C is closer to the volume 8 (where the control pulse CP is applied.) Therefore, the effect of the labeling pulse LP on the slice 2B will be greater than the effect of the control pulse CP, and the effect of the labeling pulse LP on the slice 2C will be less than the effect of the control pulse CP. Hence, the magnetization transfer effect will not be compensated for the slices 2B and 2C.

Figure 4:
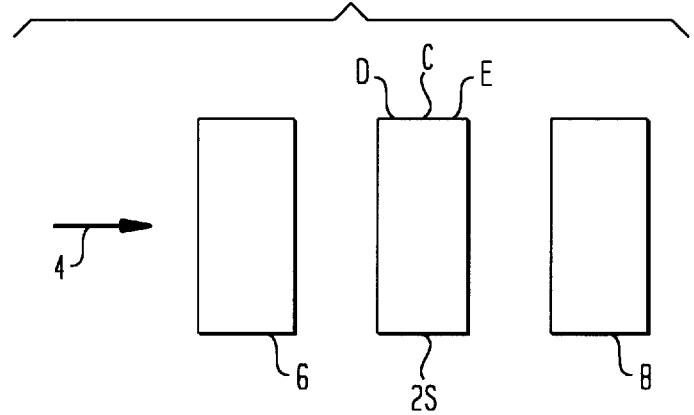
FIG. 4 schematically illustrates how a conventional magnetization transfer compensation scheme fails to compensate for magnetization transfer effects when used in a three-dimensional MR study.

The same holds true for the three-dimensional study shown in FIG. 4. In this example, a three-dimensional slab 2S is located between the volumes 6 and 8. At the center C of the slab 2S, which is equidistant from the volumes 6 and 8, the magnetization transfer effect is compensated. However, away from the center C of the slab 2S, there will always be a difference between the effect of the labeling pulse LP and the effect of the control pulse CP. In regions (e.g. region D) that are closer to the volume 6, the effect of the labeling pulse LP will predominate; in regions (e.g. region E) that are closer to the volume 8, the effect of the control pulse CP will predominate.

Figure 7A:
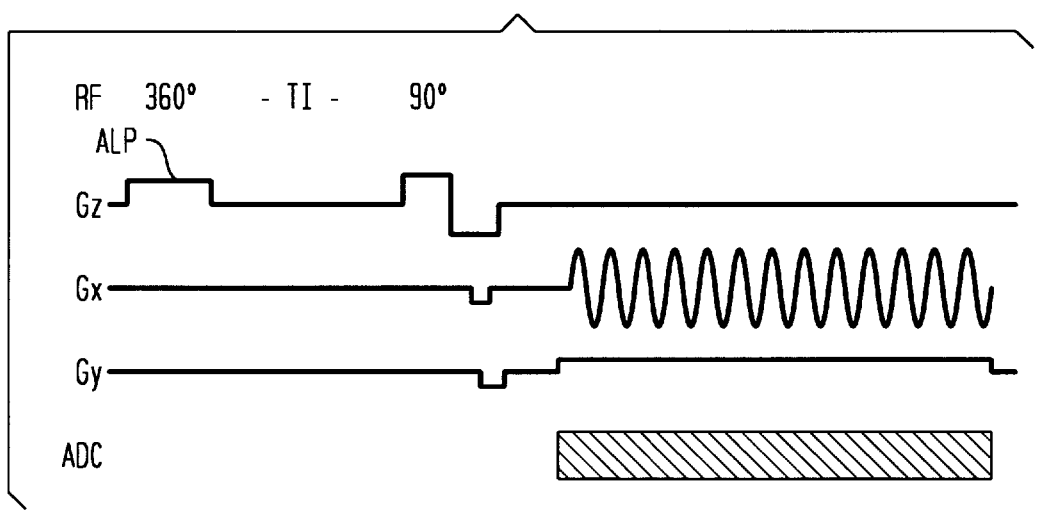
FIGS. 7A and 7B schematically illustrate, respectively, a labeling pulse and two control pulses as used in a two-dimensional MR pulse sequence in accordance with the preferred embodiment of the invention.
Figure 7B:
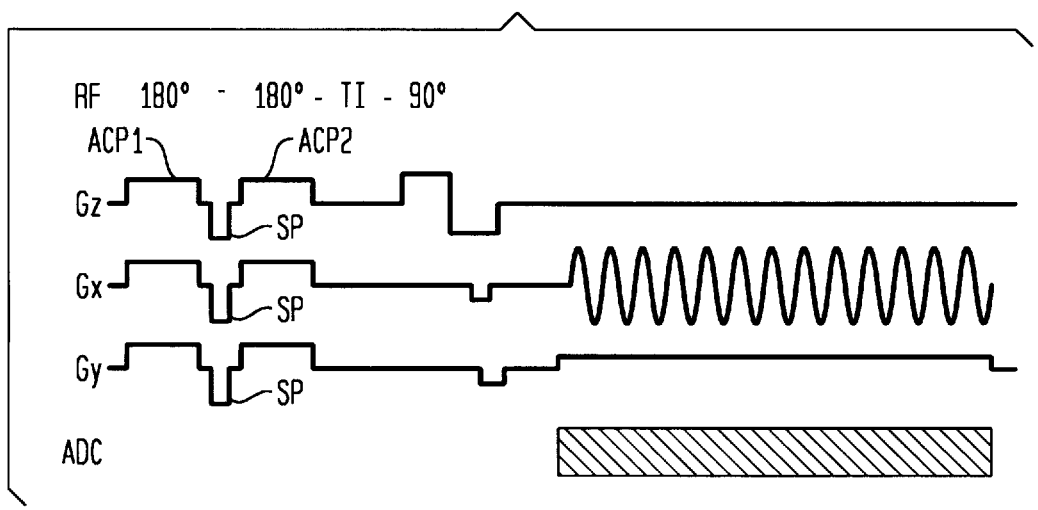

The preferred embodiment of the invention exploits characteristics of adiabatic RF pulses. An adiabatic RF pulse is an RF pulse having a power, or flip angle, exceeding 180°, but yet only inverting the spins upon which it acts. In accordance with this preferred embodiment, the labeling pulse ALP (FIG. 7A) is an adiabatic 360° pulse. And, in further accordance with the preferred embodiment, there are two control pulses ACP1 and ACP2 (FIG. 7B) that are separated by a spoiler pulse SP. Each of the control pulses is an adiabatic 180° pulse, and both are applied to the same volume 6' as the labeling pulse ALP.

Figure 5:
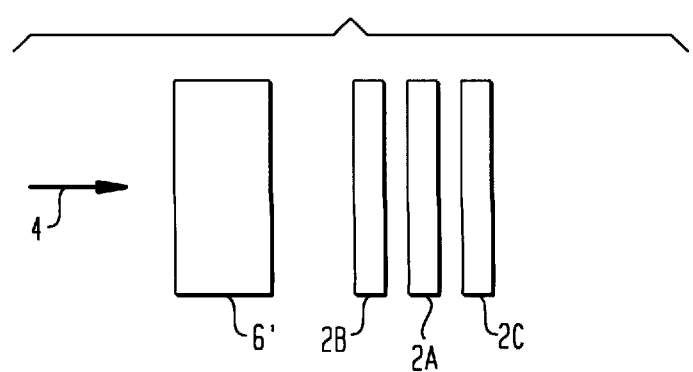
FIG. 5 schematically illustrates how the preferred embodiment of the invention compensates for magnetization transfer effects when used in a multislice MR study.
Figure 6:
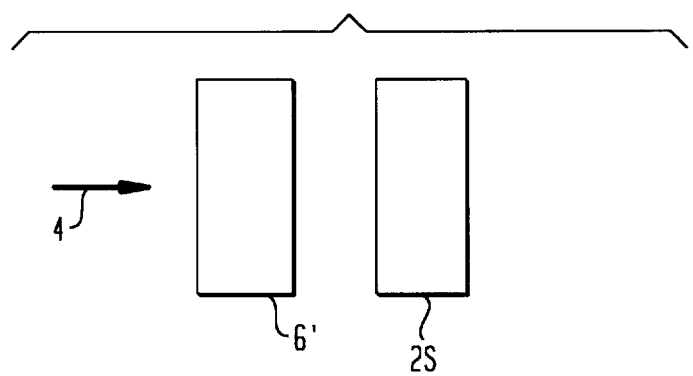
FIG. 6 schematically illustrates how the preferred embodiment of the invention compensates for magnetization transfer effects when used in a multislice MR study.

Because the total compensating flip angle, or power, of both control pulses ACP1 and ACP2 taken together (180° plus 180°) equals the flip angle (power) of the 360° labeling pulse ALP, and because all the pulses are applied to the same volume 6', the effect of the labeling pulse is everywhere the same as the cumulative effect of the two control pulses taken together. In other words, because the distance between the volume 6' and any one of the slices 2A, 2B or 2C (see FIG. 5) remains constant and is therefore the same whether a labeling pulse or a control pulse is being applied, and because the power of the labeling pulse ALP is the same as the total power of the control pulses ACP1 and ACP2, each of the slices 2A, 2B and 2C is affected the same way when a labeling pulse ALP or a pair of control pulses ACP1 and ACP2 is being applied. This compensates the magnetization transfer effect. The same is true for a three-dimensional study of a slab 2S, as is shown in FIG. 6. Furthermore, because each of the control pulses ACP1 and ACP2 is adiabatic, each only inverts the spins on which it acts. Consequently, the second control pulse ACP2 re-inverts the inflowing blood spins that have already been inverted by the first control pulse ACP1, and the net effect of the two pulses is to leave the inflowing blood spins uninverted. As a result, the second MR data acquisition occurs when uninverted blood spins have flowed into the slice, or slab, from which the MR data are being acquired.

Figure 8:
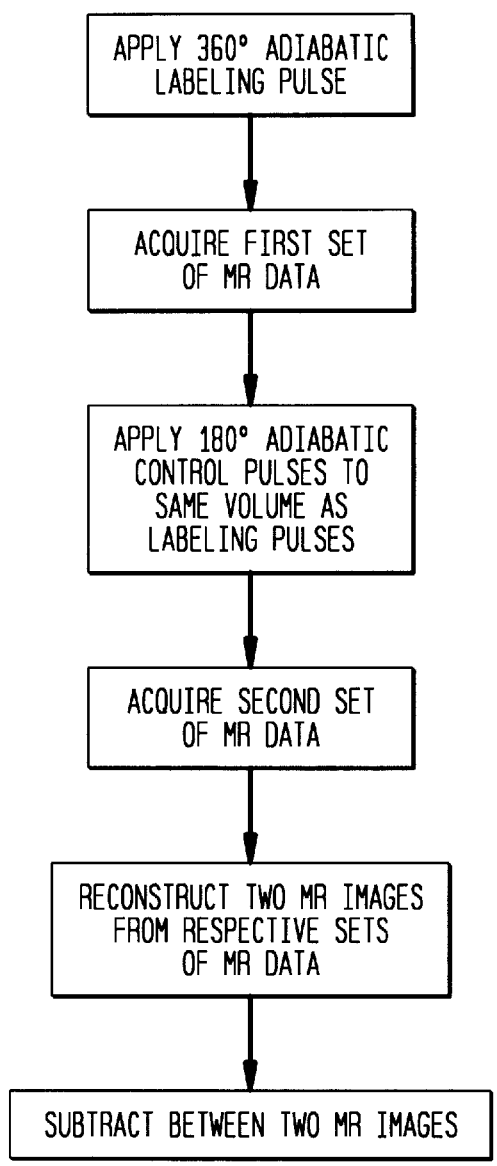
FIG. 8 is a flowchart illustrating a preferred embodiment of the invention.

Hence, in accordance with the preferred embodiment of the invention as illustrated in FIG. 8, in an initial step 50 an adiabatic 360° labeling pulse is applied to a volume upstream of the slices, or slab, to be imaged. This labeling pulse inverts the spins of inflowing blood. After a certain time, the blood reaches the slices, or slab, to be imaged. Then, in step 60, a first set of MR data is acquired. In a multislice study, the MR data are acquired using a motion-insensitive two-dimensional MR pulse sequence, such as a two-dimensional echo planar sequence; in a three-dimensional study, the MR data are acquired using a motion-insensitive three-dimensional MR pulse sequence such as a three-dimensional echo planar sequence.

Later on, in step 70, two adiabatic 180° control pulses, separated from each other by a spoiler pulse, are applied to the same volume where the labeling pulse was applied. These control pulses, taken together, have a total compensating flip angle of 360°, equalling the 360° flip angle of the labeling pulse. Consequently, the effect of the labeling pulse is everywhere the same as the total effect of the two control pulses, taken together. And, because the second control pulse undoes the spin inversion carried out by the first control pulse, the inflowing blood spins to the slices or slab are not inverted during the subsequent MR data acquisition. Thereafter, in step 80, a second set of MR data is acquired. Then, in step 90, MR images are reconstructed from the two acquired sets of MR data, and in step 100 one of the images is subtracted from the other one.

Although use of a 360° adiabatic labeling pulse and two 180° adiabatic labeling pulses is preferred, this is not necessary. As long as the total compensating flip angle of the control pulses equals the flip angle of the labeling pulse and all the pulses are applied to the same location, the invention imposes no constraint upon the number and power of the control pulses.

While one or more preferred embodiments have been described above, the scope of the invention is limited only by the following claims:

1. A method for compensating for magnetization transfer effects, comprising the following steps:

applying a labeling pulse having a predetermined flip angle to a predetermined volume of interest; and applying at least two control pulses to said predetermined volume of interest, said at least two control pulses having a total compensating flip angle equal to said predetermined flip angle.

2. The method of claim 1, wherein the control pulses follow each other successively.

3. The method of claim 2, wherein there are exactly two control pulses, each having a 180° flip angle.

4. The method of claim 1, wherein each of said at least two control pulses is an adiabatic pulse.

5. The method of claim 1, wherein the labeling pulse and said at least two control pulses are part of a two-dimensional MR pulse sequence.

6. The method of claim 1, wherein the labeling pulse and said at least two control pulses are part of a three-dimensional MR pulse sequence.

7. The method of claim 5, wherein the pulse sequence is of a motion-insensitive type.

8. The method of claim 6, wherein the pulse sequence is of a motion-insensitive type.

9. A method of conducting a multislice MRI blood flow mapping study within a volume of interest using in such a manner as to compensate for magnetization transfer effects, comprising the following steps:

using a labeling pulse to label blood within a predetermined volume that is arterially upstream of the volume of interest, said labeling pulse having a predetermined flip angle;

acquiring labeled-blood MR data from the volume of interest using an MR pulse sequence;

applying at least two control pulses to said predetermined volume, said at least two control pulses having a total compensating flip angle equal to said predetermined flip angle; and acquiring compensated-blood MR data from the volume of interest using the MR pulse sequence.

10. The method of claim 9, wherein there are exactly two control pulses, and wherein the labeling and control pulses are adiabatic.

11. The method of claim 9, wherein the MR pulse sequence is a two-dimensional multislice MR pulse sequence.

12. The method of claim 9, wherein the MR pulse sequence is a three-dimensional MR pulse sequence.

13. The method of claim 9, further comprising the steps of reconstructing a labeled-blood image of the volume of interest from the labeled-blood MR data, reconstructing a compensated-blood image of the volume of interest from the compensated-blood MR data, and comparing the labeled-blood and compensated-blood images.

* * * * *